(12) United States Patent
Woosley

(10) Patent No.: US 6,518,227 B2
(45) Date of Patent: Feb. 11, 2003

(54) SOLVENT COMPOSITION FOR DENTURE ADHESIVE

(76) Inventor: Robert Woosley, 4001 Richmond Dr. East, Jacksonville, FL (US) 32224

( * ) Notice: Subject to any disclaimer, the term of this patent is extended or adjusted under 35 U.S.C. 154(b) by 0 days.

(21) Appl. No.: 09/782,365

(22) Filed: Feb. 13, 2001

(65) Prior Publication Data
US 2002/0109123 A1 Aug. 15, 2002

(51) Int. Cl.⁷ .............................. A61K 7/16; A61K 7/30; B01F 1/00; C11D 7/50
(52) U.S. Cl. .................. 510/116; 252/364; 424/49; 510/200; 510/411; 512/5
(58) Field of Search .................. 252/364; 510/116, 510/411, 200; 512/5; 424/49; 134/40

(56) References Cited

U.S. PATENT DOCUMENTS

| | | | |
|---|---|---|---|
| 2,471,501 A * | 5/1949 | Steigleman | 252/364 X |
| 4,306,989 A * | 12/1981 | Motsenbocker | 252/364 X |
| 5,009,890 A | 4/1991 | DiPoppo | 424/195.1 |
| 5,096,709 A | 3/1992 | VanderSloot | 424/195.1 |
| 5,449,517 A | 9/1995 | Fitzjarrell | 424/195.1 |
| 5,468,473 A | 11/1995 | Mullen | 424/66 |
| 5,472,684 A * | 12/1995 | Nabi et al. | 424/49 |
| 5,558,914 A | 9/1996 | Cohen et al. | 424/59 |
| 5,610,189 A | 3/1997 | Whiteley | 514/557 |
| 5,620,695 A | 4/1997 | Elliott | 424/405 |
| 5,662,888 A * | 9/1997 | Diamond | 510/116 X |
| 5,738,863 A | 4/1998 | Sackin et al. | 424/405 |
| 5,750,108 A | 5/1998 | Edwards | 424/195.1 |
| 5,894,020 A | 4/1999 | Concha | 424/405 |
| 5,908,613 A | 6/1999 | Bozzacco | 424/50 |
| 5,948,439 A | 9/1999 | Forman et al. | 424/466 |
| 5,972,362 A | 10/1999 | Wenker | 424/407 |
| 5,998,335 A | 12/1999 | Selga et al. | 504/353 |
| 6,019,963 A | 2/2000 | Kling et al. | 424/76.1 |
| 6,379,652 B1 * | 4/2002 | Liu et al. | 424/49 |

* cited by examiner

Primary Examiner—Richard D. Lovering
(74) Attorney, Agent, or Firm—Thomas C. Saitta

(57) ABSTRACT

An oil-based solvent composition for denture adhesive, suitable for use in the oral cavity, containing Melaleuca Alternifolia oil in an oil-based carrier, such as a vegetable oil. Additional solvents such as orange oil and flavorings may be added to the composition.

15 Claims, No Drawings

SOLVENT COMPOSITION FOR DENTURE ADHESIVE

BACKGROUND OF THE INVENTION

This invention relates generally to the field of solvents, and more particularly to the field of solvents which are efficacious on gum-based denture adhesives, which are suitable for use in the oral cavity, and which comprise oil derived from the plant species Melaleuca Alternifolia.

As people age, it is quite common for people to lose all or some of their teeth due to disease or accident, resulting in problems with chewing and aesthetics. A most common solution to this problem is the use of dentures, artificial constructs of teeth mounted in a gum-receiving, generally U-shaped channel or plate which is adhered to the gums using a denture adhesive. Dentures are individually fitted to a patient by having a dentist make an impression of the patient's upper and/or lower gum line. The dentures are then manufactured to the patient's individual parameters such that the dentures mate with the patient's gum line in a secure and comfortable manner.

Denture adhesive is used to secure the dentures to the gum line for an extended time period, and can be found in powder, liquid or cream form. The adhesive is applied into the gum-receiving plate and properly positioned in the mouth. With the application of pressure, the adhesive sets or hardens and securely locks the dentures onto the gum line. As new formulations for denture adhesives have been developed, the adhesive properties have been dramatically improved—to the point where removal of the adhesive from the denture plate after the dentures are removed from the mouth for cleaning or replacement is often very difficult. Once the dentures are removed, it is also relatively difficult to remove the adhesive from the patient's gum tissue.

There are no known efficient solvents for rapid removal of the adhesive from the dentures. Under current practice, it typically require 15 to 20 minutes for a technician to physically remove the adhesive from the dentures by wiping or scrubbing them with a brush. In the patient's mouth gauze is used to scrape the adhesive from the gum tissue. This extended time period is inconvenient to the patient, and in a busy dental practice is very detrimental to maximizing patient turn-over rates.

Denture adhesive solvent technology is limited by several factors. Because of the functional environment, any solvent must first be acceptable for oral use. Because the dentures are placed into an environment where they are constantly exposed to saliva, water and other liquids, both hot and cold, the adhesives are manufactured of gum-based materials. The gum-based adhesives are by necessity highly resistant to saliva and water intrusion effects, which limits the composition of a denture adhesive to being non-water-based. Typical compositions for gum-based denture adhesives, such as that produced and sold by the Procter & Gamble Co. under the brand FIXODENT, comprise calcium/zinc polyvinyl methyl ether maleate, mineral oil, cellulose gum, petrolatum and silica, along with dyes and/or menthol, menthyl lactate or peppermint oil. Any water-based solvents will be very slow-acting on these adhesives, since the water-based solvent-resistance properties of the denture adhesive are maximized in order to extend the useful life and to increase the adhesion properties of the denture adhesive when in use in the mouth.

An object of this invention is to provide an oil-based solvent for denture adhesives, which is acceptable and suitable for use within the oral cavity, which greatly reduces the time required to loosen the adhesive bond between a denture adhesive and the denture plate and the patient's gum tissue, and further which is efficacious in quickly removing all residual adhesive from both the gum tissue and the denture plate after removal. It is a further object to provide such a solvent which may be directly applied to the denture plate and gum tissue after removal of the dentures, or provided as a rinse to be given to the patient after denture removal for swishing within the oral cavity and then expulsion. It is a further object to formulate such a solvent composition using an effective amount of Melaleuca Alternifolia oil, also commonly referred to as tea tree oil, in a vegetable or other suitable oil carrier. It is a further object to formulate such a solvent further comprising additional oils either for complementary solvent, flavoring or aromatic purposes. These and other objects not expressly set forth will be made obvious by the disclosure to follow.

The Melaleuca Alternifolia plant species is a shrub-like tree indigenous to the swampy north coastal regions of Australia, and is commonly referred as the tea tree. The oil extract from the plant contains almost 50 compounds including terpinenes, cymene, pinene, 1-trepinene-ol, terpinen 4-ol, cineole, sequiterpenes and sesquiterpene alcohols. The Australian standard requires tea tree oil to contain at least 30 weight percent terpinen 4-ol and not more than 15 weight percent cineole. The oil is typically extracted using a steam distillation technique. One kilogram of foliage typically produces between 12 and 25 grams of extract oil. Compositions containing tea tree oil are known for use as topical medications for treatment of sunburn and genital herpes, as well as for treatment of flea infestations, as muscle relaxants, antiperspirants, disinfectants, deodorants and fungicides. It is also known to use the oil in the treatment of gingivitis, in toothpaste compositions, and in-mouthwash compositions, which is significant for this application in that it demonstrates that the composition is safe for oral use.

SUMMARY OF THE INVENTION

The invention is an oil-based solvent composition which is efficacious in dissolving gum-based denture adhesives, where the solvent is effective in quickly removing residual denture adhesive from both the denture plate and the patient's gum tissue. The solvent is able to be applied directly onto the gums or the denture plate after removal of the dentures, as well as being able to be provided as a rinse to be delivered into the oral cavity, swished about by the patient and subsequently expelled.

The solvent composition comprises Melaleuca Alternifolia oil, also commonly referred to as tea tree oil, in a vegetable or other suitable oil carrier or binder, with the Melaleuca Alternifolia oil present in a volume or parts ratio to the carrier oil of preferably from approximately 1:1 to 1:18, i.e., the Melaleuca Alternifolia oil is present from about 50 to about 5 volume percent of the total carrier oil/Melaleuca Alternifolia oil total volume. The carrier oil is preferably a vegetable oil, and may be combined with other oils such as flaxseed oil. Additional solvents, flavorings and aromatics may be added to the composition.

DETAILED DESCRIPTION OF THE INVENTION

The invention is an oil-based solvent composition which is efficacious on gum-based denture adhesives, where the solvent is effective in dissolving any residual adhesive on the denture plate and the patient's gum tissue in only a few minutes. The solvent is safe for use in the oral cavity. The solvent composition is a liquid and may be formulated in various viscosities for ease of application, with a more viscous liquid being suitable for application with a cotton-tipped swab or cloth, and with a less viscous liquid being suitable for use as an oral rinse.

The solvent composition comprises Melaleuca Alternifolia oil, also commonly referred to as tea tree oil, disposed in a vegetable or other suitable oil carrier or binder, with the Melaleuca Alternifolia oil present in a volume or parts ratio to the carrier oil of preferably from approximately 1:1 to 1:18, i.e., the Melaleuca Alternifolia oil is present in the composition from about 50 to 5 volume percent of the total carrier oil/Melaleuca Alternifolia oil total volume. Most preferably, the Melaleuca Alternifolia oil is present in the composition at a volume ratio to the carrier oil of about 2:9, i.e., about 22 volume percent. Vegetable oil is preferred as the carrier oil, and in a more preferred embodiment the carrier oil is comprised of vegetable oil and flaxseed oil in a volume or parts ratio of approximately 2:1, i.e., the carrier oil is approximately 66.6 volume percent vegetable oil and approximately 33.3 volume percent flaxseed oil.

Even more preferably, additional solvent, flavoring or aromatic components are included in the composition, preferably in individual amounts approximately equal to the amount of Melaleuca Alternifolia oil. Most preferably, the carrier oil is present in an amount of approximately 75 volume percent and the Melaleuca Alternifolia oil being present in an amount of approximately 16.7 volume percent, with the remaining volume comprising one or more additives. Thus a preferred embodiment for the denture adhesive solvent composition may comprise in approximate amounts 6 parts vegetable oil, 3 parts flaxseed oil, 2 parts Melaleuca Alternifolia oil, and 1 part flavoring component, such as for example spearmint or peppermint oils. The flavoring or other aromatic component which may be added to the composition is desirable in that Melaleuca Alternifolia oil has a relatively strong and unpleasant taste, and the relative amount of the flavoring can be varied to account for varying sensitivities to unpleasant tastes. In an alternative composition, 1 part orange oil may be added as an additional solvent to the Melaleuca Alternifolia oil.

For removal of residual adhesive from the gum tissue, the solvent composition is provided as a liquid to be taken into the oral cavity and swished about, then expelled and rinsed after a few minutes, or the solvent composition may be directly applied by wiping or brushing the gum tissue with a swab or cloth containing the solvent. For removal of residual adhesive from the denture plate itself, the solvent composition is applied directly to the plate and allowed to soak the adhesive for several minutes, and then the plate is brushed, wiped or rinsed to easily remove the adhesive residue.

It is understood that certain equivalent and substitutions for certain components set froth above may be obvious to those skilled in the art, and thus the true scope and definition of the invention is to be as set forth in the following claims.

I claim:

1. A solvent composition for gum-based denture adhesives, said solvent being suitable for oral use, said solvent comprising a carrier oil and an effective amount of Melaleuca Alternifolia oil to dissolve a gum-based denture adhesive, wherein said oil-based carrier is present in approximately 50 to 95 volume percent of the total volume and said Melaleuca Alternifolia oil is present in approximately 50 to 5 volume percent of the total volume, and wherein said carrier oil comprises a vegetable oil.

2. The solvent of composition claim 1, wherein said carrier oil is a combination of vegetable oil and flaxseed oil.

3. The solvent composition of claim 2, wherein said carrier oil is composed of approximately 66.6 volume percent of vegetable oil and approximately 33.3 volume percent flaxseed oil of the total carrier oil volume.

4. The solvent composition of claim 1, wherein said carrier oil is present in approximately 78 volume percent of the total volume and said Melaleuca Alternifolia oil is present in approximately 22 volume percent of the total volume.

5. A solvent composition for gum-based denture adhesives, said solvent being suitable for oral use, said solvent comprising a carrier oil, a flavoring component and an effective amount of Melaleuca Alternifolia oil to dissolve a gum-based denture adhesive, wherein said oil-based carrier is present in approximately 50 to 95 volume percent of the total volume and said Melaleuca Alternifolia oil is present in approximately 50 to 5 volume percent of the total volume, and wherein said carrier oil is a vegetable oil.

6. The solvent composition of claim 5, wherein said flavoring component is a flavoring component chosen from the group of flavoring components consisting of peppermint oil and spearmint oil.

7. The solvent composition of claim 5, wherein said flavoring component is present in an amount approximately equal to the amount of said Melaleuca Alternifolia oil.

8. The solvent composition of claim 5, wherein said carrier oil is present in approximately 75 volume percent of the total volume, said Melaleuca Alternifolia oil is present in approximately 16.7 volume percent of the total volume, and said flavoring component is present in approximately 8.3 volume percent of the total volume.

9. A solvent composition for gum-based denture adhesives, said solvent being suitable for oral use, said solvent comprising a carrier oil, orange oil and an effective amount of Melaleuca Alternifolia oil to dissolve a gum-based denture adhesive, wherein said oil-based carrier is present in approximately 50 to 95 volume percent of the total volume and said Melaleuca Alternifolia oil is present in approximately 50 to 5 volume percent of the total volume, and wherein said carrier oil is a vegetable oil.

10. The solvent composition of claim 9, wherein said orange oil is present in an amount approximately equal to the amount of said Melaleuca Alternifolia oil.

11. The solvent composition of claim 9, further comprising a flavoring component in addition to said orange oil.

12. The solvent composition of claim 11, wherein said orange oil is present in an amount approximately equal to the amount of said Melaleuca Alternifolia oil and wherein said flavoring component is present in an amount approximately equal to the amount of said Melaleuca Alternifolia oil.

13. A process for removing gum-based denture adhesive from a surface, comprising the steps of:

applying to a gum-based denture adhesive a solvent for dissolving said gum-based denture adhesive, said solvent being suitable for oral use and comprising a carrier oil and an effective amount of Melaleuca Alternifolia oil to dissolve said gum-based denture adhesive;

allowing said gum-based denture adhesive to dissolve; and removing said gum-based denture adhesive from said surface.

14. The process of claim 13, wherein said step of applying said solvent is performed within a person's oral cavity.

15. The process of claim 13, wherein said step of removing said gum-based denture adhesive is accomplished by wiping.

* * * * *